United States Patent [19]

Essex et al.

[11] Patent Number: 4,725,669
[45] Date of Patent: Feb. 16, 1988

[54] ASSAY FOR DETECTING INFECTION BY HUMAN T-CELL LYMPHOTROPIC VIRUS-III

[75] Inventors: Myron E. Essex, Sharon, Mass.; Tun-Hou Lee, Stockholm, Sweden

[73] Assignee: President and Fellows of Harvard College, Cambridge, Mass.

[21] Appl. No.: 670,361

[22] Filed: Nov. 9, 1984

[51] Int. Cl.$^4$ ............... C07C 103/52; C07G 7/00
[52] U.S. Cl. .................. 530/322; 530/395; 530/829
[58] Field of Search ........... 260/112 R, 112 B; 436/504, 510, 515, 518, 528, 531, 533, 536–546, 804, 808–811, 813, 823, 547, 548; 435/4, 5, 7, 810, 948; 424/86, 89, 101; 514/8, 908, 931; 530/300, 322, 350, 395, 829

[56] References Cited

U.S. PATENT DOCUMENTS 4,520,113  5/1985  Gallo et al. ............... 436/504
4,524,027  6/1985  Bohn ........................ 424/101

OTHER PUBLICATIONS

Robey et al, "Prospect for Prevention of Human Immunodeficiency Virus Infection: Purified 120-kDa Envelope Glycoprotein Induces Neutralizing Antibody", *Proc Natl Acad Sci USA*, vol. 83, pp. 7023–7027, Sep. 1986.
Allan et al, "Major Glycoprotein Antigens that Induce Antibodies in AIDS Patients are Encoded by HTLV-III", *Science*, vol. 228, 1091–1093, 1985.
Berin et al, "Virus Envelope Protein of HTLV-III Represents Major Target Antigen for Antibodies in AIDS Patients", *Science*, vol. 228, 1094–1096, 1985.
Potocnjak et al., Science, vol. 215, 1637–1639 (1982).
Schupbach et al., Science, vol. 224, 503–505 (1984).

*Primary Examiner*—John Kight
*Assistant Examiner*—Nathan M. Nutter

[57] ABSTRACT

A first glycoprotein having a molecular weight of approximately 120,000 daltons in the H9/HTLV-III cell line, of which approximately 90,000 daltons is the unglycosylated moiety, is obtained from cells infected with human T-cell leukemia virus, type III. A second glycoprotein having a molecular weight of approximately 160,000 daltons is also obtained from such cells, of which approximately 90,000 daltons is the unglycosylated moiety and is substantially identical to the unglycosylated moiety of the first glycoprotein.

The presence, in a biological specimen, of either of these glycoproteins or of the unglycosylated moiety is indicative of the presence of cells infected by human T-cell leukemia virus. An assay for the glycoprotein or its unglycosylated moiety is a useful diagnostic procedure for determining such infection in biological specimens.

10 Claims, 3 Drawing Figures

ASSAY FOR DETECTING INFECTION BY HUMAN T-CELL LYMPHOTROPIC VIRUS-III

This invention was made with Government support, and the Government has certain rights in the invention.

BACKGROUND OF THE INVENTION

This invention relates to novel purified forms of glycoprotein found in the cell surface membrane of cells infected with human T-cell leukemia virus, type III (HTLV-III), and to an assay for detecting in biological specimen the presence of an antibody to the antigenic determinants present in said glycoproteins.

HTLV-III is suspected of playing a key role in the pathogenesis of the acquired immunodeficiency syndrome (AIDS). It has been shown that human patients whose bodies contain antibodies to HTLV-III-infected cells are apparently latently or actively infected with the virus.

SUMMARY OF THE INVENTION

It has now been found that particular polypeptides or glycoproteins present on the cell surface of human cells infected with HTLV-III, when purified and isolated, contain an antigenic determinant or determinants which provide a high degree of sensitivity and immunospecificity for antibody to human cells infected with HTLV-III. Consequently, the substantially pure glycoproteins or their unglycosylated moieties are useful as a diagnostic tool for assaying biological specimens to determine whether they contain cells which have been infected by HTLV-III. Other polypeptides containing immunologically cross-reactive antigenic determinants are useful for the same purpose. By "polypeptides containing immunologically cross-reactive antigenic determinants" is meant polypeptides having in common antigenic determinants with which a given antibody will react. Such other polypeptides include the unglycosylated moieties of the glycoproteins. Other useful polypeptides or proteins, which have the necessary immunogenic determinants, include synthetic polypeptides. They also include antibodies or fragments thereof which are anti-idiotypic towards the active determinant or determinants on the glycoprotein of the invention. It has also been shown that anti-idiotypic reagents are useful as diagnostic tools for the detection of antigens carrying sites which are immunologically cross-reactive with those on the antibodies (Potocnjak et al., Science 215: 1637–1639 (1982) herein incorporated by reference). Thus, an assay for HTLV-III infected cells could be carried out with the aid of an anti-idiotypic antibody or immunologically active fragment thereof which carries an antigenic site or sites thereon which are immunologically similar to the antigenic site or sites on the glycoprotein of the invention. Such anti-idiotypic antibodies can be raised against first antibodies having specificity against the antigenic sites on the glycoprotein of the invention (i.e. the anti-idiotypic antibodies are anti-antibodies). Preferably monoclonal anti-idiotypic antibodies are used.

An assay for HTLV-III infection is important because the virus can be readily transferred from the peripheral blood leukocytes of antibody-positive people to leukocytes of antibody-negative people when the two are cultivated together. Popovic et al., Science, Vol. 219, 856–859 (1983). Consequently, it appears that there is great risk of infection involved in whole blood transfusions when the transfused blood contains infected cells. The assay is of importance because biological specimens from individuals exhibiting acquired immunodeficient syndrome (AIDS) give a positive test for antibodies to the antigenic determinant of the novel glycoprotein, thus facilitating diagnosis of that disease.

Consequently, the invention also embraces the method of assaying a biological specimen for the presence of antibody to HTLV-III-infected cells which comprises incubating said specimen with a polypeptide having an antigenic determinant or determinants immunologically cross-reactive with those of a first glycoprotein having a molecular weight of approximately 120,000 daltons (gp120), of which approximately 90,000 daltons is the unglycosylated moiety (p90), or with a second glycoprotein having a molecular weight of approximately 160,000 daltons (gp160) of which the 90,000 dalton unglycosylated moiety is substantially identical to the unglycosylated moiety of the first glycoprotein, which glycoproteins occur on the cell surface of cells infected with HTLV-III, and determining whether or not an immunocomplex is formed between said antibody and said polypeptide.

The invention also embraces a method of assaying a biological specimen for the presence of antigenic determinant or determinants immunologically cross-reactive with the determinants of the glycoproteins of molecular weight 120,000 daltons, or 160,000 daltons. The determinants to be assayed may occur on the stated glycoproteins themselves or on other polypeptides. They may be in free circulation in the body fluids or in lymphocytes. The assay can be carried out by known immunoassay methods, using antibodies, monoclonal or polyvalent, having immune reactivity with the antigenic determinants found on the stated glycoproteins. For example competitive immunoassays or immunometric (sandwich) assays can be used. In the drawings, FIG. 1 represents an autoradiogram showing specific activities of gp120 and gp160 as determined by gel electrophoresis;

FIG. 2 represents an autoradiogram showing specific activities of gp120 and gp160 as determined by gel electrophoresis; and FIG. 3 represents an autoradiogram illustrating specific activity of p90 as determined by gel electrophoresis.

DESCRIPTION OF THE PREFERRED EMBODIMENTS

Figures 1, 2, 3:
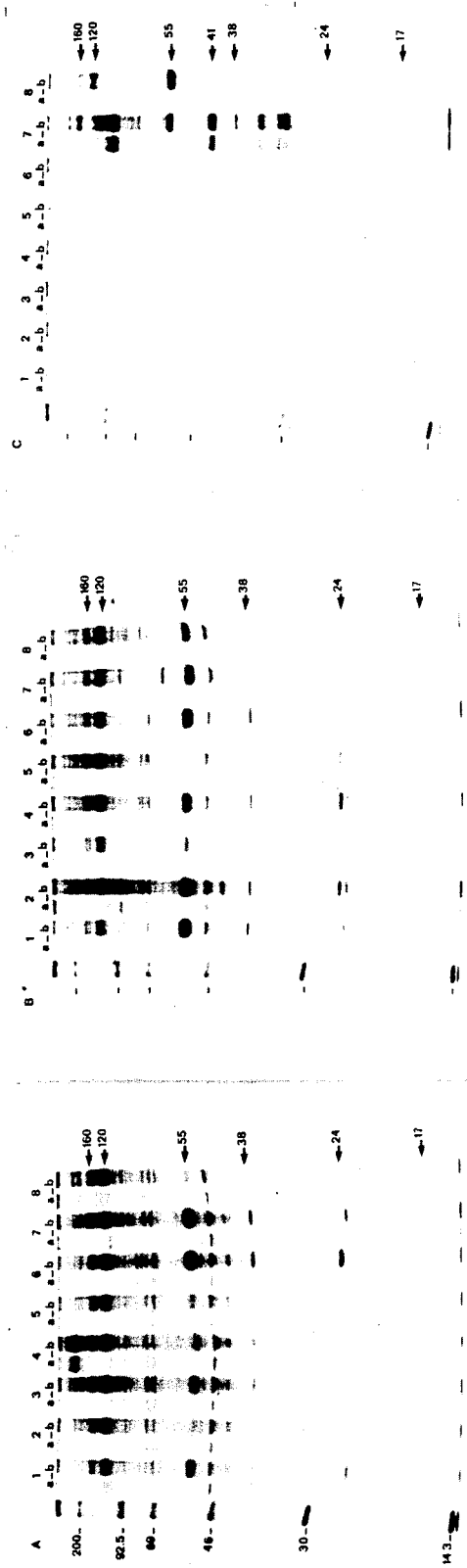
Figure 3:
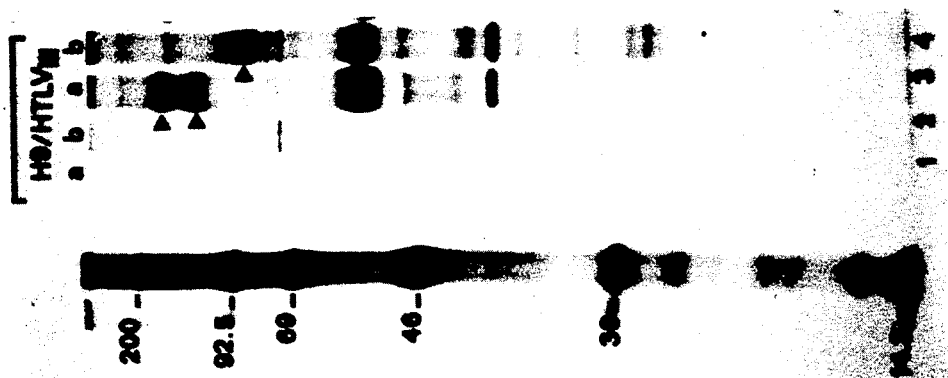
Figure 2:
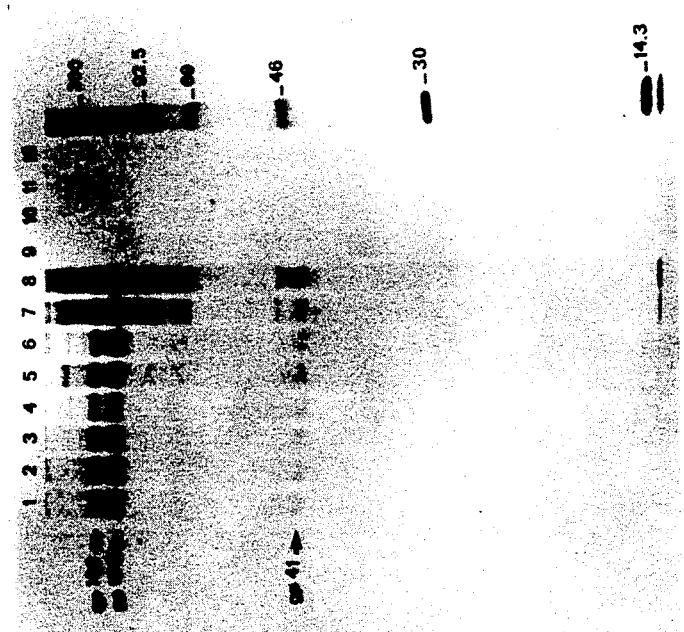
Figure 4:
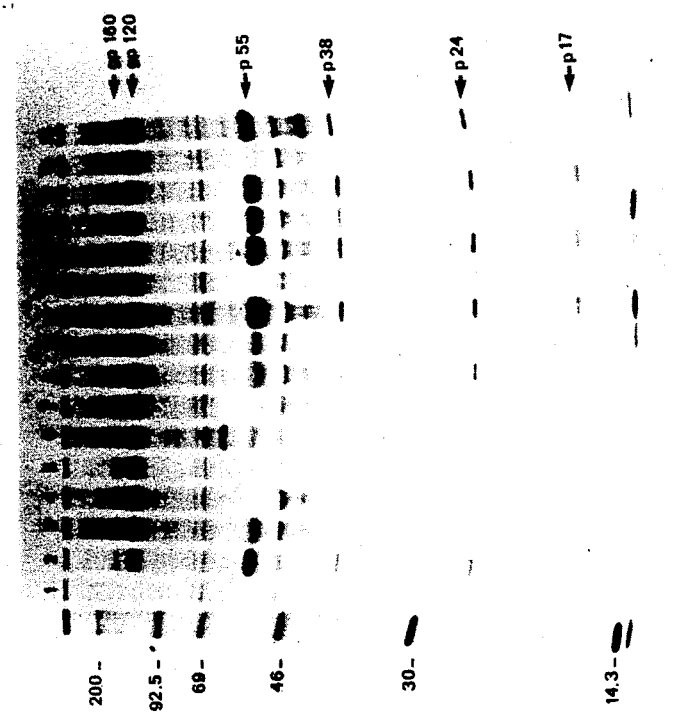

The glycoproteins of the present invention have a molecular weight of approximately 120,000 daltons and approximately 160,000 daltons as determined by sodium dodecyl sulfate (SDS) gel electrophoresis and are soluble in SDS buffer consisting of 0.15M sodium chloride, 0.05M Tris hydrochloride PH 7.2, 1% Triton X-100, 1% sodium deoxycholate, 0.1% sodium dodecylsulfate, and 1 mM phenylmethylsulfonyl fluoride. Triton X-100 is a nonionic detergent (octylphenoxy polyethoxy (9–10) ethanol). The unglycosylated moiety of the 120,000 dalton and of 160,000 dalton glycoprotein has a molecular weight of approximately 90,000 daltons and contains substantially the same antigenic determinant or determinants as do the glycoproteins themselves.

The glycoproteins can be obtained from HTLV-III-infected cells. A variety of cell lines have been prepared, which are permanently and persistently infected with HTLV-III; among them can be mentioned HTLV-III-infected H9 cells, Lymphadenopathy Associated Virus-(LAV) infected NC37 cells, and Molt 3 and HUT 78 cells infected with fresh AIDS virus isolates. It may be that the exact sizes of the novel glycoproteins are slightly different in different lines; however, the common immunologically cross reactive portion of the glycoproteins is the same regardless of cell line, since it is a protein induced by HTLV-III. Thus, any cell which harbors the virus may be an appropriate source for the novel glycoproteins. In order to obtain the protein from any infected cells carrying the virus, the cells are metabolically labelled (e.g. with $^{35}$S-cysteine) and immunoprecipitated with antisera obtained from HTLV-III-infected subjects. The novel glycoproteins can then be detected and isolated by gel electrophoresis. By "HTLV" as used in the present specification and claims it is meant to include the virus generically. Thus any and all forms, subtypes, or variations of the virus are included.

For example, the glycoproteins are present at the cell surfaces of the HTLV-III infected human T-cell line H9, LAV-infected NC37 cells, and Molt 3 and HUT 78 cells infected with fresh AIDS virus isolates. The glycoproteins can readily be separated from the cells of these cell lines by lysis thereof and SDS gel electrophoresis.

The purified and isolated glycoproteins or any antigen immunologically cross-reactive therewith can be employed as a standard antigen in any conventional assay procedure for detection in biological specimens of the presence of antibodies specific thereto, hence of the presence in the specimen of cells infected with HTLV-III and/or symptomatic of AIDS. The antibodies specific to such HTLV-III antigens are not found in patients suffering from diseases such as hepatitis which are not accompanied by HTLV-III infection.

The glycoproteins or polypeptides immunologically cross-reactive therewith can be labelled by conventional procedures with $^{125}$I or $^{35}$S or $^3$H for use in radioimmunoassay, with fluorescein for fluorescent immunoassay, with enzyme for enzyme immunoassay or with biotin, for biotin-avidin linked assays. It can be employed labelled or unlabelled as desired, in competitive immunoassays, as well as in double antibody assays using two antibodies, either of the idiotype:antiidiotype variety or more particularly of the second antibody type using an anti-Fc antibody, or other assays.

Alternatively, the novel glycoproteins or polypeptides immunologically cross-reactive therewith could be immobilized on an insoluble phase, such as an insoluble resin, and detection of the anti-glycoprotein antibodies is carried out by measuring their binding to the insoluble phase. Insoluble phases also include latex particles, which when coated with the novel glycoprotein or its immunologically cross-reactive polypeptides and subjected to anti-glycoprotein antibody, will agglutinate. Yet other insoluble phases include test tubes, vials, titration wells, and the like, to which the novel glycoprotein or its immunologically cross-reactive polypeptide can be bound, and antibody thereto detected by double antibody techniques or Protein-A dependent techniques.

The assay for antibodies which recognize HTLV-III-induced cell surface antigens may utilize the glycoprotein or glycoproteins or the unglycosylated moiety of MW 120,000 daltons, 160,000 daltons and 90,000 daltons respectively in crude form, and is not limited to using these proteins in substantially pure form. For example, the glycoprotein(s) may be first substantially purified and then mixed together. Alternatively cruder mixtures can also be used.

The elements necessary for carrying out the diagnostic methodology described hereinbefore may be present in a kit. Such kit comprises a carrier being compartmentalized to receive therein one or more containers, which of said containers comprising one or more elements necessary to carry out the tests.

For example, the first container may contain one or both of the purified glycoproteins or its immunologically cross-reactive polypeptides in detectably labelled or in insolubilized form.

A second container may comprise anti IgG antibody, polyclonal or monoclonal, useful in double antibody binding assay, or elements needed for detection of the label on the glycoprotein or its immunologically cross-reactive polypeptides (e.g. chromogenic substrates).

Additional containers may comprise varying amounts of one of the glycoproteins or its immunologically cross-reactive polypeptides which can be used to prepare a standard curve into which experimental results can be interpolated. The materials may be present in the kit by themselves, in solution, freeze dried, or in admixture with other inert materials, such as inert proteins, and the like.

The biological specimens tested may include blood, serum, lymphocytes, urine, tissues, saliva, feces, and the like. Of particular interest is the screening of blood in blood banks, to assure that the blood is not contaminated with HTLV-III. Screening of blood-derived products, such as vaccines, can also be done by the methods of the invention.

The following specific examples are intended to illustrate more fully the nature of the invention without acting as a limitation upon its scope.

Characterization of Proteins

The reactivity of serum samples positive for antibodies to HTLV-III induced cell membrane antigens (HTLV-III-MA) was determined by RIP-SDS-PAGE, the proteins being separated on a 12.5% SDS-polyacrylamide gel with 3.5% stacking gel using the Laemmli buffer system.

Uninfected H9 cells (a), and H9 cells infected with HTLV-III(b) at their peak log phase of growth were harvested and exposed to [$^{35}$S]-cysteine (100 µCi/ml; specific activity 957.5 Ci/mmole) for 14-16 hours. A soluble cell lysate was obtained and cleared once with a reference negative control serum bound to Protein A Sepharose CL4B (Protein A beads) as described by Essex et al., (1983) Science 220:859, before portions were reacted with 8 µl of the following sera preabsorbed with Protein A beads with the results shown in FIG. 1 of the drawing: (A) sera from 8 AIDS patients that were positive for anti-HTLV-III-MA (lanes 1-8), (B) sera from 4 ARC patients that were positive for anti-HTLV-III-MA (lanes 1-4) and sera from 4 healthy homosexuals that were positive for anti-HTLV-III-MA (lanes 5-8); (C) sera from 2 healthy homosexuals that were negative for anti-HTLV-III-MA (lanes 1-2), sera from 2 laboratory workers that were negative for anti-HTLV-III-MA (lanes 3-4), a mouse monoclonal antibody to p24 of HTLV-III (lane 5), a normal rabbit serum (lane 6), a reference rabbit antiserum to disrupted HTLV-III (lane 7), and a positive control ARC patient (lane 8). The molecular weight markers were $^{14}$C-labeled myosin (200,000), phosphorylase-b (92,500), bovine serum albumin (69,000), ovalbumin (46,000), carbonic anhydrase (30,000) and lysozyme (14,300).

Preparation of Labeled Glycoprotein

H9 cells infected with HTLV-III at their peak log phase of growth were harvested and exposed to [$^{35}$S]-cysteine (100 μCi/ml; specific activity 957.5 Ci/mmole) for 14–16 hours. To enrich glycoprotein fractions, the soluble cell lysate was first reacted with lentil lectin sepharose 4B at a ratio of $20 \times 10^6$ cells to 1 ml of lentil lectin 4B at 4° C. for 3 hours. Deoxycholate-free RIPA buffer in the presence of 5% methyl αD mannoside was used to elute the glycoprotein fraction. The glycoprotein fraction was analyzed using RIP-SDS-PAGE with human sera positive for anti-HTLV-III-MA. The [$^{35}$S]-cysteine labeled glycoproteins were reacted with 8 μl of the following sera with the results shown in FIG. 2: 4 sera from 4 AIDS patients positive for anti-HTLV-III-MA (lanes 1–4), 2 sera from 2 ARC patients that were positive for anti-HTLV-III-MA (lanes 5–6), 2 sera from 2 healthy homosexuals that were positive for anti-HTLV-III-MA (lanes 7–8), 2 sera from healthy homosexuals that were negative for anti-HTLV-III-MA (lanes 9–10), and 2 sera from 2 laboratory workers that were negative for anti-HTLV-III-MA (lanes 11–12).

Preparation of Labelled Unglycosylated Moiety of Glycoprotein

HTLV-III infected H9 cells at their peak log phase of growth were harvested and resuspended in McCoy's 5A medium supplemented with 10% fetal bovine serum, 1% of antibiotic-antimycotic mixture, and 20 μg/ml of tunicamycin for 2 hours. After this trimming step, the cells were labelled with [$^{35}$S]-cysteine as described above in the presence of 20 μg/ml of tunicamycin for 3 hours. The labelled material was then subjected to the same lysing and preclearing procedures as described above. The proteins from treated and untreated cells were analyzed by human sera positive for anti-HTLV-III-MA using RIP-SDS-PAGE as shown in FIG. 3, left hand lane. Soluble cell lysates from tunicamycin-untreated (a) and - treated cells (b) were reacted with: 8 μl of a reference serum negative for antibodies to HTLV-III (lanes 1–2) and 8 μl of a reference serum positive for antibodies to HTLV-III from an ARC patient (lanes 3–4), with the results shown in FIG. 3.

Cell Line Deposits

The following cell lines have been deposited with the American Type Culture Collection (ATCC) in Rockville, Md.:

| Cell Line | ATCC Accession Number |
| --- | --- |
| NC 37 | CCL 214 |
| HUT 78 | TIB 161 |
| MOLT-3 | CRL 1552 |
| H9 | CRL 8543 |

What is claimed is:

1. A substantially pure polypeptide having an antigenic determinant or determinants immunologically cross-reactive with determinants of a first glycoprotein having a molecular weight of approximately 120,000 daltons, said glycoprotein having substantially the same antigenic determinants as a second glycoprotein having a molecular weight of approximately 160,000 daltons, of which approximately 90,000 daltons is the molecular weight of the unglycosylated moiety, said glycoproteins being obtained from cells infected with human T-cell lymphotrophic virus-III.

2. The polypeptide of claim 1 which is the first or second HTLV-III-associated cell surface glycoprotein of claim 1, 3. A polypeptide as claimed in claim 1 which comprises the unglycosylated moiety of the first or second HTLV-III-associated glycoprotein of claim 1.

4. A polypeptide as claimed in claim 1 which is obtained from HTLV-III infected H9 cells, from LAV infected NC37 cells, from Molt 3 cells, or from HUT 78 cells.

5. A polypeptide as claimed in claim 1 which comprises an anti-idiotypic antibody having an antigenic determinant which is immunologically cross-reactive with said first glycoprotein.

6. A polypeptide as claimed in any of claims 1, 2, or 3 which is detectably labelled.

7. The polypeptide of any of claims 1, 2 or 3 which is bound to an aqueous-insoluble phase.

8. The substantially unglycosylated moiety of the second glycoprotein of claim 1.

9. The moiety as claimed in claim 8 which is detectably labelled.

10. The moiety as claimed in claim 8 which is bound to an aqueous-insoluble phase.

* * * * *